(12) United States Patent  
Barea

(10) Patent No.: US 7,773,225 B2  
(45) Date of Patent: Aug. 10, 2010

(54) DEVICE FOR THE OPTICAL ANALYSIS, INCLUDING TWO-DIMENSIONAL, OF A THREAD OR YARN

(76) Inventor: Tiziano Barea, Via Valle Olona, 17, 21052 Busto Arsizio (Varese) (IT)

( * ) Notice: Subject to any disclaimer, the term of this patent is extended or adjusted under 35 U.S.C. 154(b) by 617 days.

(21) Appl. No.: 10/597,318

(22) PCT Filed: Jan. 27, 2005

(86) PCT No.: PCT/EP2005/050351

§ 371 (c)(1),
(2), (4) Date: Jul. 20, 2006

(87) PCT Pub. No.: WO2005/078384

PCT Pub. Date: Aug. 25, 2005

(65) Prior Publication Data

US 2008/0225305 A1    Sep. 18, 2008

(30) Foreign Application Priority Data

Feb. 16, 2004    (IT) .......................... MI2004A0252

(51) Int. Cl.
*G01N 21/84* (2006.01)

(52) U.S. Cl. ...................................... 356/429; 356/430

(58) Field of Classification Search .......... 356/429–431
See application file for complete search history.

(56) References Cited

U.S. PATENT DOCUMENTS

| 4,341,958 A | | 7/1982 | Ohsawa et al. | |
|---|---|---|---|---|
| 4,739,176 A | * | 4/1988 | Allen et al. | 250/559.45 |
| 5,424,557 A | * | 6/1995 | Rydborn | 250/559.01 |
| 6,201,602 B1 | * | 3/2001 | Bouvyn | 356/238.1 |

FOREIGN PATENT DOCUMENTS

| EP | 0 117 571 A1 | 9/1984 |
|---|---|---|
| EP | 1 359 108 A1 | 11/2003 |
| JP | 63-185900 A | 11/1988 |
| JP | 64-043700 | 2/1989 |
| JP | 2-5238 B | 2/1990 |
| JP | 07-189598 | 7/1995 |
| JP | 2003-206698 | 7/2003 |
| JP | 2004-019181 | 1/2004 |
| JP | 2005-076310 | 3/2005 |
| WO | WO 99/35075 A | 7/1999 |
| WO | PCT/JP2004/011200 | 11/2004 |

* cited by examiner

*Primary Examiner*—Michael P Stafira
(74) *Attorney, Agent, or Firm*—Cozen O'Connor

(57) ABSTRACT

A device for the optical analysis, including two-dimensional, of a thread or yarn (F) fed to a textile machine, said device comprising at least one light emitter element (3, 4) and at least one receiver element (5), said emitter element (3, 4) generating a light signal which strikes said thread (F) before being sensed by the receiver element (5) which, based on this sensing, defines a characteristic of the thread (F) such as its movement or its stoppage, a dimensional defect or another dimensional characteristic, between said light emitter element (3, 4) and said receiver element (5), there being interposed light transparent means (6) which are encountered by the light signal after it has interacted with the thread (F), and which act as a thread guide.

10 Claims, 5 Drawing Sheets

DEVICE FOR THE OPTICAL ANALYSIS, INCLUDING TWO-DIMENSIONAL, OF A THREAD OR YARN

FIELD OF THE INVENTION

The present invention relates to a device for the optical analysis of a thread or yarn in accordance with the introduction to the main claim. In particular, the invention relates to a device for monitoring its count variation and the possible presence of foreign bodies, and for analyzing its profile.

BACKGROUND OF THE INVENTION

Methods and devices for monitoring threads or yarns are well known, they using various technologies, for example capacitive or optical piezoelectric sensors.

Piezoelectric sensor devices, for example that described in EP 0117571, use for example a piezoelectric ceramic combined with a textile ceramic or other element for contact with the thread or yarn, to transmit vibrations, caused by the roughness of the yarn sliding on said element, to the piezoelectric ceramic. The main advantage of this technology is its almost absolute insensitivity to the presence of dirt or yarn residues in contact with the textile ceramic, the yarn itself automatically cleaning the point of contact with the ceramic.

However, this technology presents the main drawback of the absolute need for physical contact between the thread or yarn and the textile ceramic with which the piezoelectric ceramic is combined; this prevents monitoring of yarns which, for example, cannot be touched during their monitoring, to prevent undesired friction or rubbing, which could tear the thread or modify a controlled characteristic, such as tension.

Another drawback is the sensitivity of the piezoelectric ceramic to the presence of very intense vibrations or noises which by simulating the condition of the thread in its sliding state would prevent the device, in case of yarn breakage, from generating the signal for halting the textile machine.

In contrast, capacitive sensor devices measure the capacitance variation of said sensors caused by the variation in their dielectric, including the actual yarn subjected to monitoring. By measuring the variation in said dielectric, the state of movement the thread, its possible count variation, etc. can be measured. The advantage of this technology is the ability to monitor a yarn even without direct contact with it, the presence of dirt or yarn residues only slightly influencing the measurement capacity of said sensors.

The main drawback of these devices is however the impossibility of monitoring conductive threads or yarns, such as copper or steel threads or those in which carbon fibres are present; in the same manner, moist yarns or those wetted with water or treated with antistatic or conductive oils cannot be monitored. This is because a conductive thread or yarn or the presence of water would short-circuit the dielectric, hence making it impossible to measure and monitor the yarn.

Moreover the capacitive means present high sensitivity to electrical fields or electrostatic discharges, the presence of which could be mistaken for a moving thread condition, which often prevents its correct operation.

In contrast, optical sensor devices, see for example that described in EP 0519281, normally use a light transmitter and a receiver, between which the thread or yarn to be monitored is positioned.

The main advantage of this technology is the ability to monitor any type of thread or yarn, whether conductive or not, without any contact with it. The disadvantage of the technology is mainly its sensitivity to the formation of dirt and residues left by the monitored yarn on the receiver and/or transmitter.

OBJECTS AND SUMMARY OF THE INVENTION

An object of the present invention is to provide an optical sensor device which offers all the major advantages of the three different aforedescribed technologies, i.e. monitoring of any type of thread or yarn, whether conductive or not, monitoring achieved without any contact with the thread or yarn if necessary, insensitivity to the formation of dirt or yarn residues, insensitivity to the presence of conductive oils or more simply water, insensitivity to vibration, noise sources, electrical fields, etc.

Another object is to provide a device of the stated type which is of simple and economical construction.

Another object is to provide a device of the stated type, the form and ergonomics of which enable it to be used in any field of the textile machine sector or other sectors, for example for monitoring machines producing copper coils, motor windings, or oil transformers.

Another object is to provide a device of the stated type which also combines within itself the thread guide function necessary for guiding the thread.

Another object is to provide an optical device of the stated type in which the area sensitive to variation in the image of the yarn profile and/or position is as large as possible, being much larger than the dimensions of the sensitive areas of the photosensitive element used, and enabling any thread or yarn monitoring application to be satisfied with great flexibility.

A further object is to provide a device of the stated type which is sealed and able to operate without problems under very severe applicative conditions.

A further object is to provide a device enabling two-dimensional analysis of the monitored thread.

These and further objects which will be apparent to the expert of the art are attained by a device in accordance with the accompanying claims.

BRIEF DESCRIPTION OF THE DRAWINGS

The present invention will be more apparent from the accompanying drawing, which is provided by way of non-limiting example, and in which.

DETAILED DESCRIPTION OF THE INVENTION

With reference to said figures, a device constructed in accordance with the present invention is indicated overall by 1 and comprises two infrared light transmitter elements 3 and 4 positioned at an angle to each other, and a receiver element 5 which can be a photodiode, phototransistor, a PSD, etc. The transmitter elements 3 and 4 are preferably orientated towards the centre of the receiver element.

The device 1 also comprises means 6 transparent to infrared light, such as a textile ceramic for example formed of zirconium, also acting as a thread guide. Within the means 6 there moves, fed to a textile machine (not shown), a thread F the movement of which is to be monitored, in order to halt said machine should the thread break, and prevent the machine from continuing to produce articles (formed from a plurality of threads fed thereto) which would inevitably be imperfect and have to be rejected.

The light transparent means act as a thread guide while at the same time preventing dirt or powder from depositing on the receiver element 5 and altering its operability. These means also increase the operability of the receiver element 5 by incrementing in a controlled manner the light beam which strikes them, to increment each striking shadow cone generated by the thread F encountered by the light emitted by the transmitter elements 3 and 4.

Figure 3:
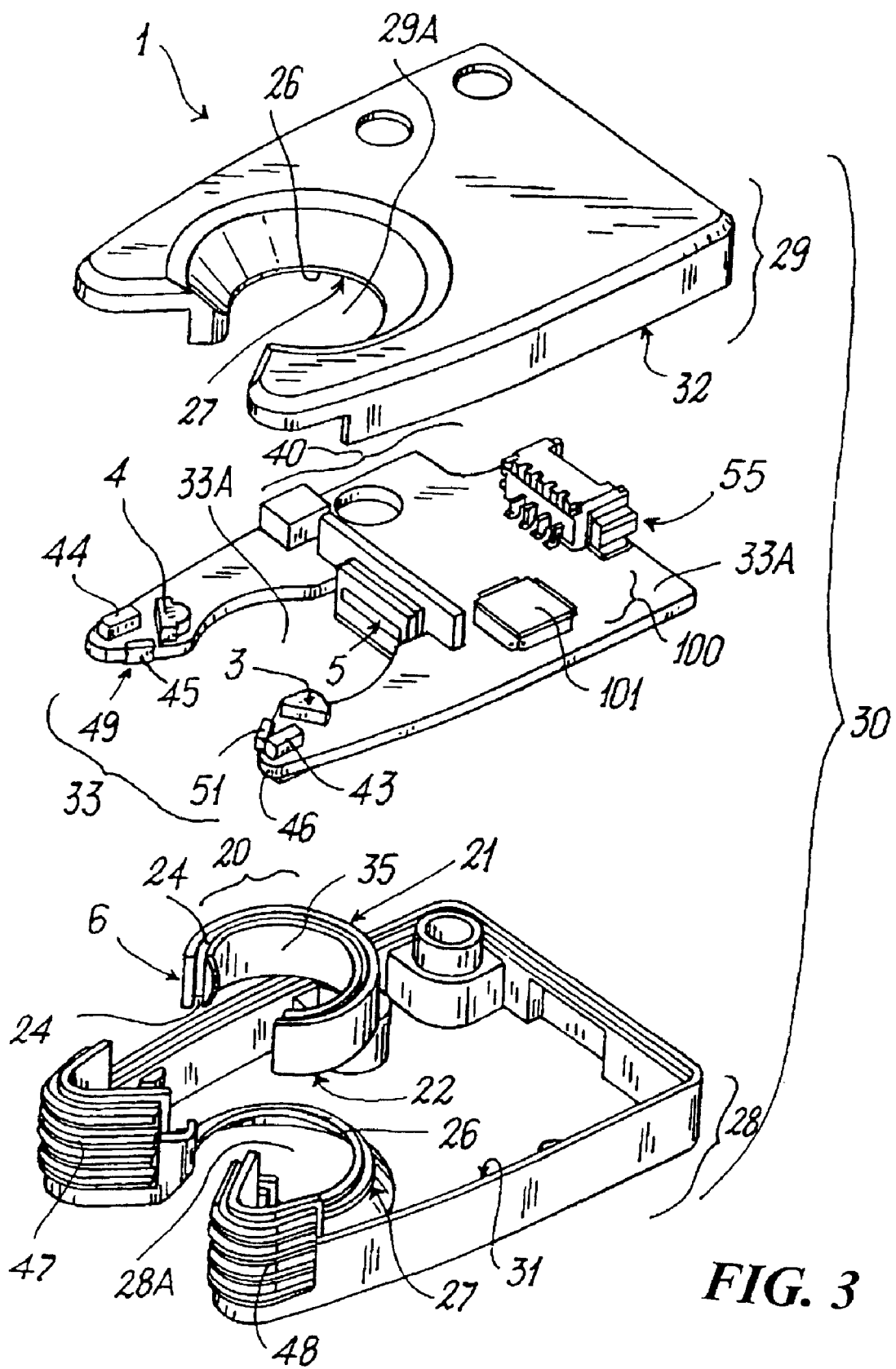
FIG. 3 is an exploded perspective view of an embodiment of the device according to the present invention.

The elements 3, 4 and 5 are associated with an electronic circuit 100 comprising a microprocessor unit 101 (FIG. 3). The circuit 100 is of known type.

It will be assumed that the light transmitter elements 3 and 4 are activated simultaneously: this causes the formation of two separate shadow cones 10 and 11, relative to the cross-section of the thread F, which strike the receiver element 5. This generates, in known manner, an electrical signal proportional to the thread cross-section.

It will now be assumed that the thread moves within the light transparent means 6 and slides inside the sensitive area of the receiver element 5 or, while maintaining its position, it varies its cross-section (a totally usual occurrence because however perfect the thread or yarn, it still differs at each of its points): this sliding or cross-section variation causes in known manner a variation in the position and/or shape of the shadow cones 10 and 11 striking the receiver element 5, to cause a variation in the electrical signal generated thereby. This signal is known to be a function of the image and/or position variation of the monitored yarn.

Because of the presence of more than one light transmitter element 3, 4, a very large image-sensitive area on the receiver element 5 is obtained, enabling easy and reliable monitoring of a thread or yarn to be achieved independently of the position of the thread F inside this sensitive area, because in whatever position the thread F lies within the light transparent means 6, the yarn is always encountered by the light emerging from at least one of the elements 3 and 4, hence the element 5 continuously senses its presence (via its shadow or the sensed light reflection by said element 5).

The light transparent means 6 also enable the thread to be contained within and if necessary guided into this sensitive area. This element, besides being transparent to IR light, is also of wear resistant material and hence suitable for remaining if necessary in contact with the thread without being damaged. It should be noted that these means can either always be in contact with the thread F or be usually separated from it when fed to a textile machine by unwinding from a suitable support (bobbin), the term "usually" meaning that purely occasional transient contact can occur with the means 6 during this feed.

Contact between the thread and said means 6 also results in natural and automatic cleaning of said means, hence as stated making the device 1 insensitive to the formation of dirt or yarn residues: they cannot accumulate because the light transparent means are cleaned by the yarn as it slides.

In a variant, the transmitter elements 3, 4, instead of being operated simultaneously, can be operated alternately to obtain a read-off signal as neither shadow cone (for example the cone 10 generated by the transmitter element 4) is reduced by the illumination provided by the non-operating transmitter element (in the example, the transmitter element 3). This enables a device of even better performance to be obtained, especially if the device 1 is not used simply to analyze the state of movement of the yarn F, but also for other purposes such as analysis and measurement of the yarn count or cross-section.

Figure 1:
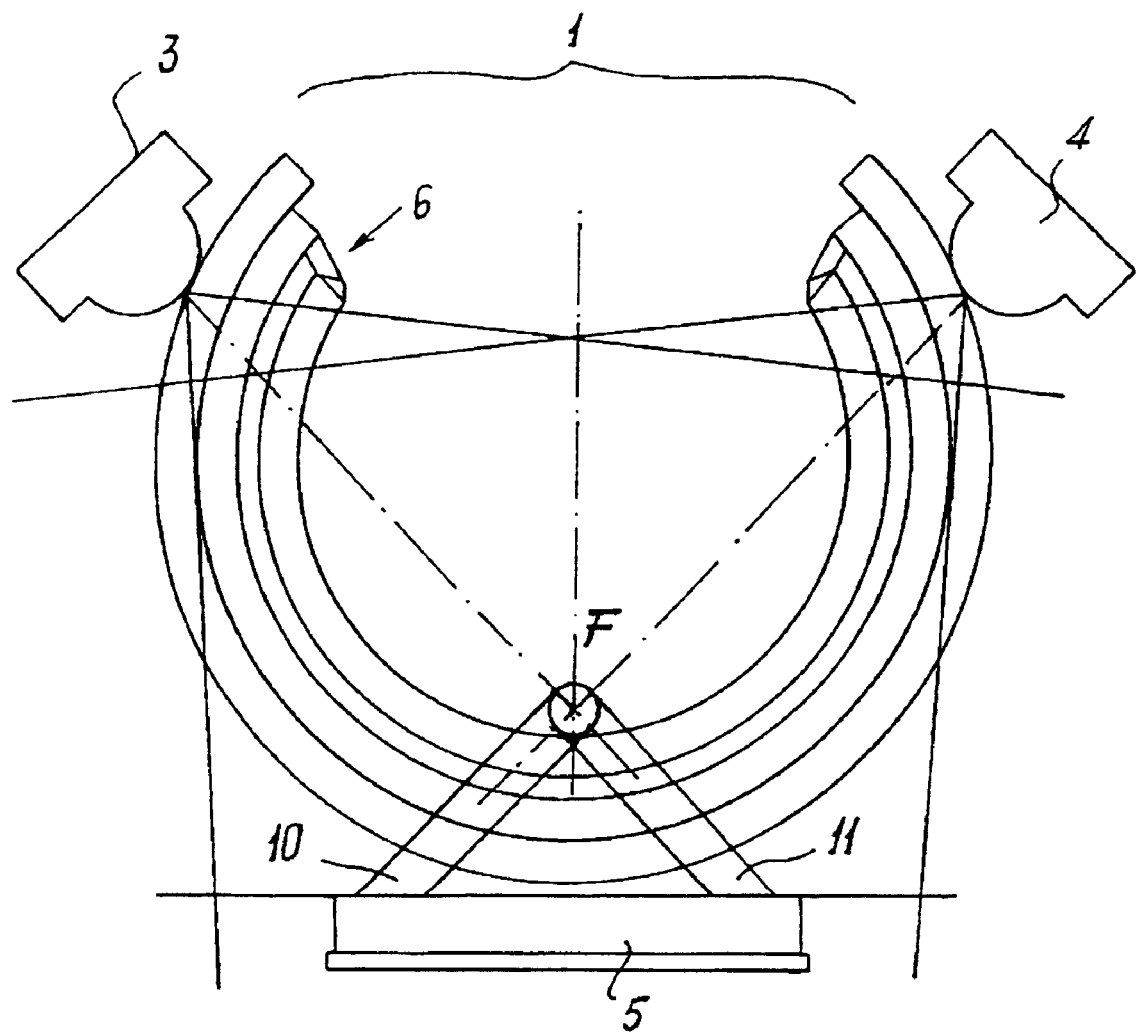
FIG. 1 represents schematically a device of the invention showing the spatial position of the transmitter and receiver elements when applying illumination for direct reading of the variation in position and/or image.
Figure 2:
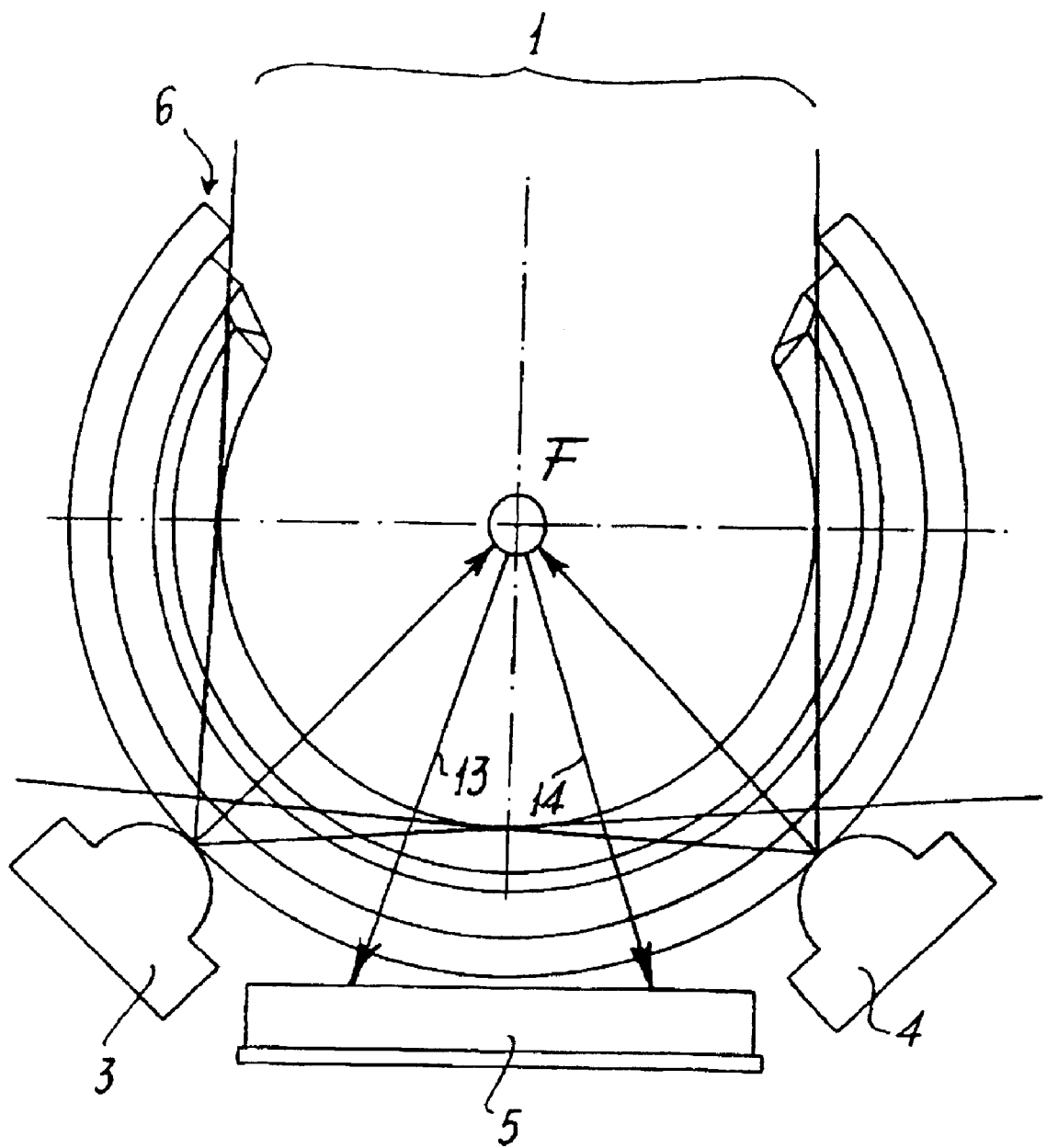
FIG. 2 represents a different embodiment of the device of the invention showing the spatial position of the transmitter and receiver elements when applying illumination for reading the variation in position and/or image by reflection.

Alternatively, with reference to FIG. 2 (in which parts equal to those of FIG. 1 are indicated by the same reference numerals), the device 1 can use two receiver elements 3 and 4, the transmitted light of which, after passing through the transparent means 6 containing and guiding the yarn, encounters the monitored thread or yarn F and is reflected towards the receiver element 5 (as indicated by the arrows 13 and 14). This latter, struck by said light, generates an electrical signal proportional to the light quantity reflected.

Again in this case the light transparent means 6 could be activated either simultaneously or alternately.

In a simplified version, the device 1 could use only one light emitter, 3 or 4, or could use a reflection element (mirror type) in a position opposite the transmitter elements 3 and 4 of FIG. 2, to obtain a mixed configuration between the solutions proposed in FIGS. 1 and 2.

In a further more complex variant, the transmitter elements could be more than two in number, for example four or more, to further increase the sensitive area of the receiver element 5.

Figure 4:
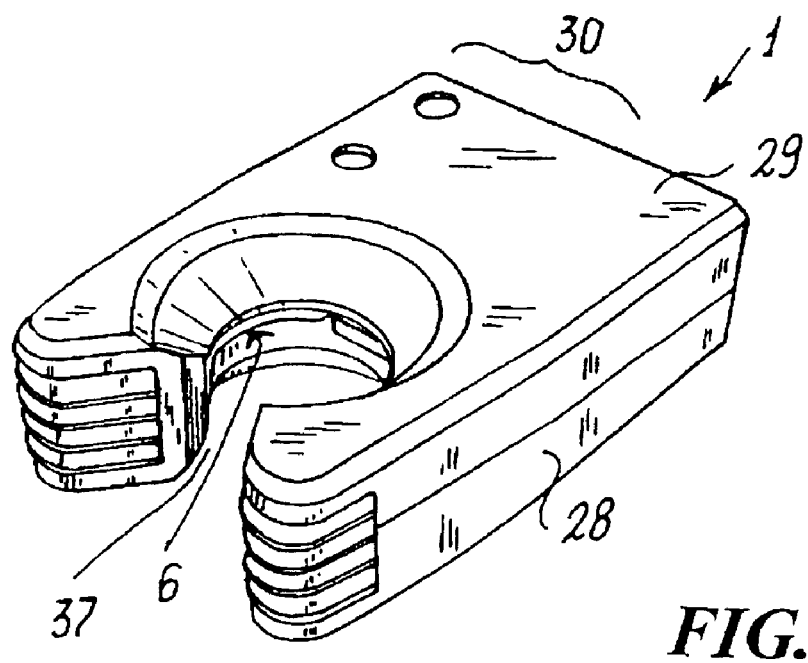
FIG. 4 is a front perspective view of the device of FIG. 3 assembled.
Figure 5:
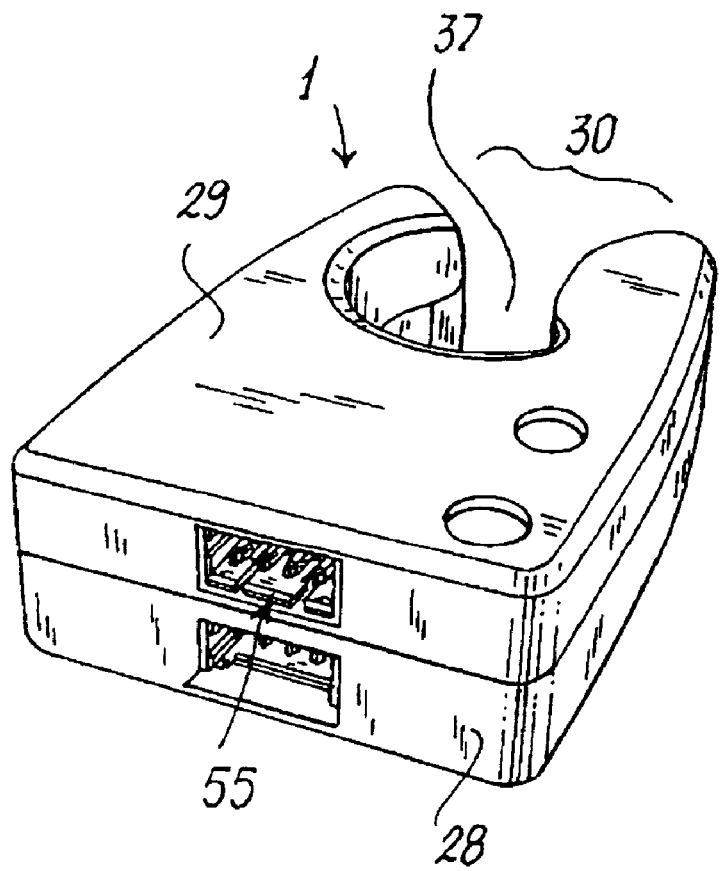
FIG. 5 is a rear perspective view of the device of FIG. 3 assembled.

FIGS. 3, 4 and 5 show a possible embodiment of the device 1 in accordance with the teachings of the present invention. In these figures, parts corresponding to those of the already described figures are indicated by the same reference numerals.

The figures show the infrared light transmitter elements 3 and 4, for example KINGBRIGHT type, code No. K3010F3C, and the light transparent means 6, for example of alumina, zirconium, sapphire or synthetic ceramic, or similar material, which also act as a thread guide; in a more economical form, these means 6 could be of simple plastic, of nylon, polycarbonate or other type, or glass.

The light transparent means 6 comprise a body 20 which, in the example, is in the form of an open ring. The body 20 comprises opposing edges 21 and 22 in which recesses 24 are provided to receive shoulders 26 projecting from a portion 27 for supporting parts 28 and 29 of the casing 30 of the device 1. These parts are to be closed one on the other (see FIGS. 4 and 5) to retain between them the elements 3, 4, 5 and an electronic circuit 40 connected to these elements.

The parts 28 and 29 fit together along the opposing edges 31 and 32, which are preferably formed (in known manner with projections and corresponding recesses) such as to co-penetrate and enable the parts to be fixed together. Fixing means such as screws or the like (not shown) can also be provided or the connection can be made permanent by glue positioned along the edges 31 and 32 or by ultrasound bonding.

A substantially flat support 33 carrying the elements 3, 4, 5 and the circuit 40 is disposed between the parts 28 and 29. This support is retained by said parts when they are fixed together.

The parts 28, 29 and the support 33 have an open portion (28A, 29A, 33A respectively) corresponding to the aperture 35 in the body 20 of the light transparent means 6. In the figures these open portions and said aperture 28A, 29A, 33A and 35 have a substantially circular shape open on one side where they define a corridor 37 for inserting the thread F into the aperture 35 for its monitoring.

The body 20 could however be of different shapes or dimensions; instead of an open ring shape to facilitate insertion of the thread F as in the example shown in FIG. 3, it could be of closed ring shape if required to contain the rotary movement (ballooning) of a yarn being unwound from a bobbin or if a yarn is to be monitored during a twisting or spiralling process.

FIG. 3 shows the receiver element 5, which can be a position sensor PSD produced by the known firm HAMAMATSU, code No. 7105-05. Two LEDs 43 and 44 (for example red and green) are also shown for indicating a fault or "all OK" respectively. These LEDs are located on arms 45 and 46 of the support 33, extending from a main portion 33A of this latter, in positions corresponding with windows 47 and 48 in the part 28 of the casing 30 which, like the part 29, is preferably formed like the support 33 with regard to said arms.

In a position corresponding with the LED 43 there is located an IR light transmitter, for example of SUNLED code No. ZTNI54W type, with a phototransistor receiver 51, for example of SUNLED code No. ZRMI54W type, located in a position corresponding with the LED 44; this transmitter and receiver pair form an optical key or barrier which if interrupted, for example by insertion of the operator's index finger, momentarily turns off the device. Another interruption of this barrier again turns on the device. This optical key could be advantageously used to reset an alarm signal, or an acceptance signal for the communication address code, etc.

Finally, FIG. 3 shows a feed connector 55 for input and output signals to and from the device 1; for example, these signals can be used respectively for serial communication between the device 1 and the electronic control circuit of the textile machine to which the thread F is fed, for the stop signal for said machine if irregularities such as yarn breakage are present, or in the case of irregularities such as a count variation (for example because of knots, entanglements or extraneous fibres); or again, during twisting or when two yarns are combined by winding one yarn (like a spiral) round the other, if count variations are present caused by two or more troughs where the number of twists measured differs from the set parameter.

These functions can be activated by the device 1 via its circuit 100 and the unit 101 which can be connected via the connector 55 to the electronic control circuit of the textile machine.

The circuit 100 is formed and operates in the following manner.

Figure 6:
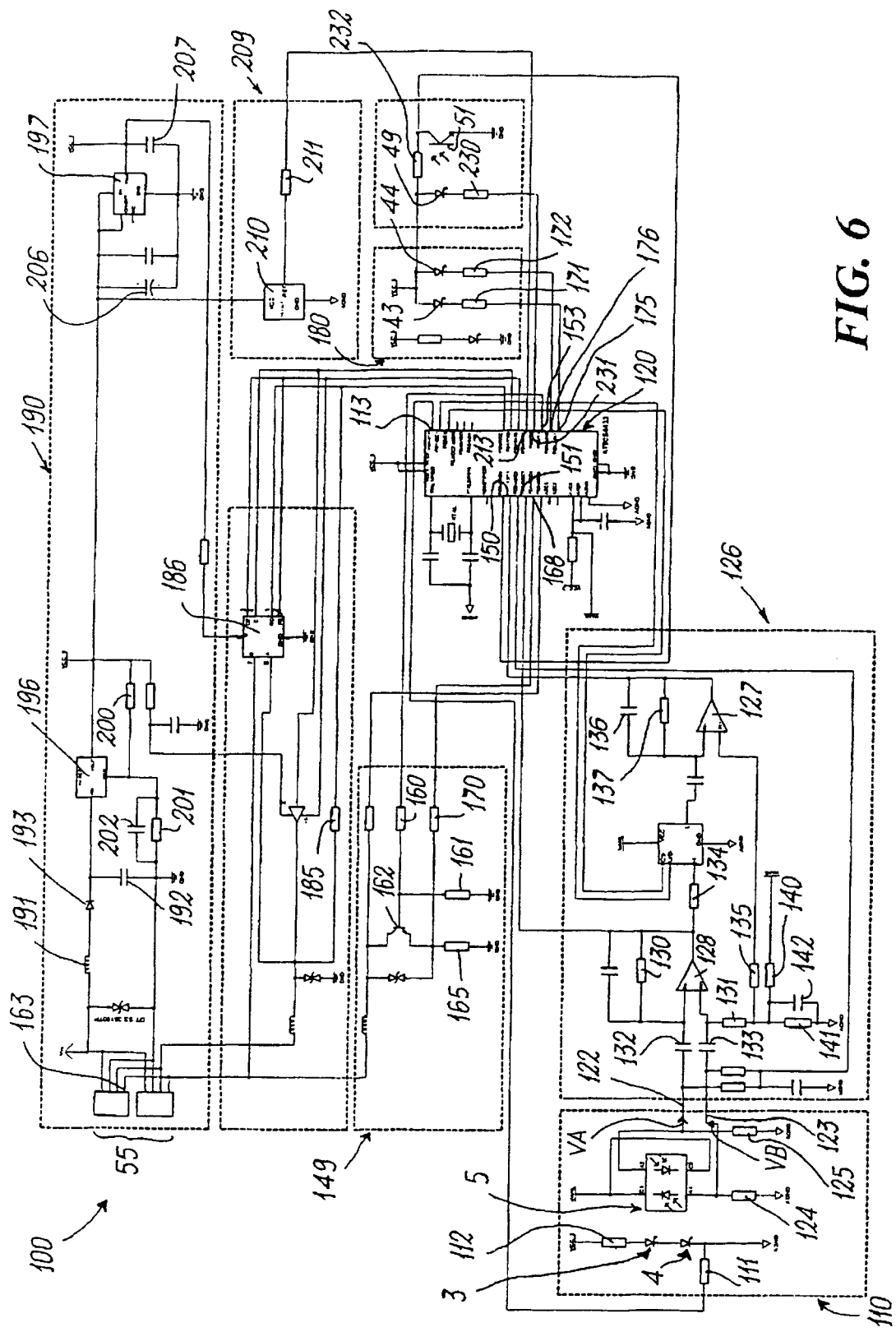
FIG. 6 shows a circuit schematic of the device of FIG. 1.

With reference to FIG. 6, the electrical schematic of a device formed in accordance with the present invention comprises, in the example, an optical position sensor 110 identified by a known PSD circuit. It is used to intercept the direct (FIG. 1) or reflected (FIG. 2) image, this image consisting of modulation of the infrared light emitted by transmitter elements 3 and 4 defined by photodiodes. These diodes are biased by the biasing current defined by the biasing resistors 111 and 112.

A microprocessor unit (or simply microcontroller) 120 is provided connected to the resistor 111 via its gate 113. The unit or microcontroller 120 can reduce the value of the current passing through the diode 3, when the system is under stand-by or low consumption conditions.

When the PSD sensor 110 is struck by infrared light based on the image of the monitored thread or yarn, it generates at its output terminals (photodiode anodes) two currents based on the position in which the infrared light image (yarn profile) strikes the PSD optical sensor.

These currents polarize resistors 124 and 125, which enable a potential difference to be generated across the resistors, to enable voltage signals VA and VB to be emitted at the outputs 122 and 123 of the sensor 110.

A two stage amplifier circuit 126, formed from operational amplifiers 127 and 128 and relative biasing networks comprising resistors and capacitors 130, 131, 132, 133, 134, 135, 136 and 137, receives the signals VA and VB. The circuit 126 presents a reference signal obtained from the resistors 140 and 141 and from a filter capacitor 142; this circuit arrangement enables a differential amplifier to be formed able to amplify the potential differences present across the already described resistors 124 and 125, i.e. the signals VA and VB leaving the sensor 110.

The circuit 126 generates suitably amplified signals leaving the two stage amplifier and directed to the gates 150 and 151 of the unit 120. These amplified signals, for example equal to 1000 and respectively 100 times the image variation level sensed at the inputs of said two stage differential amplifier, result in a device with a double control scale.

The amplified signals present at the gates 150 and 151 of the microcontroller 120 are converted in known manner from analog signals to digital signals by the ADC unit forming part of said unit 120.

Said conversion enables the previously amplified signals to be converted into numerical values which are a function of the image relative to the monitored yarn; by means of a processing algorithm they are able to define whether the image variation has values in terms of levels and frequencies which are equal to or greater than the programmed minimum reference value.

If the image variation level and frequency values are less than the programmed reference value for an abnormality time exceeding a programmable "alarm time" value, an alarm signal is generated leaving the gate 150 of the unit or microcontroller 120. This signal is fed to a protection/alarm block 149.

By way of biasing resistors 160 and 161 the signal from said gate 153 operates the output transistor 162, which activates a (current) alarm signal present at the (STOP) input 163 of the connector.

A resistor 165 is used as a shunt resistor to enable the current operated by the transistor 162 to be measured, the voltage drop across the resistor being a function of the current generated by the transistor.

This voltage drop is measured by the unit 120 via the gate 168 connected via a decoupling resistor 170 to the resistor 165. This protects the STOP output of the device 1 against short-circuits: in this respect, in the case of high current exceeding the defined maximum value, the unit 120 deactivates the transistor 162 to protect it.

A diode 170, connected in parallel with the transistor 162, also acts as protection against voltage inversions between the collector and emitter of said transistor 162.

Via the respective biasing resistors 171 and 172 connected to the respective outputs 175 and 176 of the unit 120, the LEDs 43 and 44 enable abnormalities of the device 1 to be indicated; an activated green light LED 43 indicates "all OK" whereas an activated red light LED 44 indicates an abnormality in the intercepted yarn. These LEDs 43 and 44 and their related resistors form an abnormality sensing block 180 for the device 1.

The device 1 can be connected to a programming/communication unit for programming parameters relating to image variation level limits and relative alarm times, which if exceeded cause the device to activate the STOP output and the red alarm LED.

Said communication takes place via a suitable input and an appropriate output of the unit 120 interfaced with the connector 55 via an input decoupling resistor 185 and an output buffer 186 respectively.

A power circuit 190 is also present, formed by known L-C low pass filters 191 and 192, by a protection diode against feed polarity inversion 193, and by stabilizer circuits 196 and 197. The first stabilizer has relative biasing components 200 and 201 and a filter 202, the values of which predetermine the stabilized output voltage of the stabilizer 196, identified by VCC5 and fixed at 5V. The second stabilizer 197, pertaining to a second power stage at 3.3V, comprises anti-disturbance filters consisting of capacitors 206 and 207.

A power reset circuit 209 is also provided consisting of a stabilizer 210 connected to a resistor 211 connected to a gate 213 of the unit 120, by which this latter obtains correct data control and saving in case of network abnormalities or holes.

Finally, the circuit 100 comprises the photodiode transmitter 49 (biased by the resistor 230 and piloted by the unit 120 via the gate 231) and phototransistor receiver 51 with relative biasing resistor 232; as stated, these form an optical key interruption barrier, the activation state of which can be read by the unit by reading the relative input at the gate 113. This optical key can be used for example as a RESET key for the yarn monitoring device of the invention.

The invention claimed is:

1. A device for the optical analysis of a thread or yarn (F) fed to a textile machine, said device comprising at least one light emitter element (3,4) and at least one receiver element (5), said emitter element (3,4) generating a light signal which strikes said thread (F) before being sensed by the receiver element (5) which, based on this sensing, defines a characteristic of the thread (F) such as its movement or its stoppage, a dimensional defect or another dimensional characteristic, wherein, interposed between said light emitter element (3,4) and said receiver element (5), light transparent means (6) which are encountered by the light signal after it has interacted with the thread (F), and which act as a thread guide, wherein said light transparent means (6) are of ceramic material and are transparent to infrared light so that the light emitted is not diffused, and wherein the light emitter elements (3,4) are at least two in number and are oriented such that the thread (F) is always struck by the light emitted by at least one of them.

2. A device as claimed in claim 1, wherein said ceramic material contains at least one of the following: alumina, zirconium, sapphire, that is the ceramic material is a transparent textile ceramic.

3. A device as claimed in claim 1, wherein said light transparent means (6) are in contact with the thread (F).

4. A device as claimed in claim 1, wherein the light transparent means (6) comprise an at least partly annular body (20), the monitored thread (F) being positioned within the aperture (35) of this body, said body (20) being supported by the device casing (30) which is shaped such as to lie at least partly about said aperture (35) of said body (20) of the light transparent means (6).

5. A device as claimed in claim 4, wherein its casing (30) comprises two coupled-together parts (28,29) which retain between them the body (20) of the light transparent means (6).

6. A device as claimed in claim 5, wherein the parts (28,29) of its casing (30) present opposing edges (31,32) able to be fitted together, within said parts (28,29) there being positioned an electrical circuit (100) presenting the at least one light emitter element (3,4) and the receiver element (5), this latter being connected to a microprocessor unit (120) arranged to evaluate each monitored characteristic of the thread (F), in accordance with a preset algorithm on the basis of the light signal received by the receiver element (5).

7. A device as claimed in claim 6, wherein the parts (28,29) of its casing (30) and the support (33) present arms projecting from a main portion and at least partly defining the body (30) of the light transparent means.

8. A device as claimed in claim 7, wherein said arms are mutually opposing and define a corridor (37) in the casing (30) of the device (1).

9. A device as claimed in claim 8, wherein on the opposing arms there are positioned a light transmitter element (49) and a receiver element (51) which act as an optical barrier arranged to modify, when intercepted, the activity state of the device (1).

10. A device as claimed in claim 9, wherein on at least one of said opposing arms there is positioned a light transmitter element (3,4) directed towards the receiver element (5).

* * * * *